(12) United States Patent
Verser et al.

(10) Patent No.: US 7,601,865 B2
(45) Date of Patent: Oct. 13, 2009

(54) RECOVERY OF ORGANIC ACIDS

(75) Inventors: Dan W. Verser, Golden, CO (US); Timothy J. Eggeman, Lakewood, CO (US)

(73) Assignee: ZeaChem, Inc., Golden, CO (US)

( * ) Notice: Subject to any disclaimer, the term of this patent is extended or adjusted under 35 U.S.C. 154(b) by 340 days.

(21) Appl. No.: 11/046,206

(22) Filed: Jan. 28, 2005

(65) Prior Publication Data

US 2005/0256337 A1  Nov. 17, 2005

Related U.S. Application Data

(60) Provisional application No. 60/540,606, filed on Jan. 29, 2004, provisional application No. 60/550,659, filed on Mar. 5, 2004, provisional application No. 60/570,134, filed on May 10, 2004.

(51) Int. Cl.
*C07C 62/00* (2006.01)
*C07C 51/42* (2006.01)
*C07B 53/00* (2006.01)

(52) U.S. Cl. .............. 562/508; 562/600; 562/606; 562/608

(58) Field of Classification Search ............ 562/600, 562/508, 608, 606
See application file for complete search history.

(56) References Cited

U.S. PATENT DOCUMENTS

| | | |
|---|---|---|
| 1,421,605 A | 7/1922 | Steffens |
| 2,079,414 A | 5/1937 | Lazier |
| 2,565,487 A | 8/1951 | Filachione et al. |
| 2,782,243 A | 2/1957 | Hess et al. |
| 3,678,118 A | 7/1972 | Frampton et al. |
| 3,686,334 A | 8/1972 | Britton |
| 3,769,329 A | 10/1973 | Paulik et al. |
| 3,878,261 A | 4/1975 | Gardner |
| 3,956,482 A | 5/1976 | Hahn et al. |
| 4,055,590 A | 10/1977 | Gruber et al. |
| 4,100,189 A | 7/1978 | Mercier |
| 4,113,662 A | 9/1978 | Wall |
| 4,134,926 A | 1/1979 | Tsao et al. |

(Continued)

FOREIGN PATENT DOCUMENTS

GB    933714    8/1963

(Continued)

OTHER PUBLICATIONS

Busche et al., *Recovery of Acetic Acid from Dilute Acetate Solution*, Biotechnology and Bioengineering Symp. No. 12, 249-262 (1982).

(Continued)

*Primary Examiner*—Taylor Victor Oh
(74) *Attorney, Agent, or Firm*—Sheridan Ross P.C.

(57) ABSTRACT

A method is disclosed for the recovery of an organic acid from a dilute salt solution in which the cation of the salt forms an insoluble carbonate salt. A tertiary amine and $CO_2$ are introduced to the solution to form the insoluble carbonate salt and a complex between the acid and an amine. A water immiscible solvent, such as an alcohol, is added to extract the acid/amine complex from the dilute salt solution to a reaction phase. The reaction phase is continuously dried and a product between the acid and the solvent, such as an ester, is formed.

35 Claims, 4 Drawing Sheets

U.S. PATENT DOCUMENTS

| | | | |
|---|---|---|---|
| 4,140,799 A | 2/1979 | Nagodawithana et al. | |
| 4,206,036 A | 6/1980 | Takeuchi et al. | |
| 4,275,234 A | 6/1981 | Baniel et al. | |
| 4,282,323 A | 8/1981 | Yates | |
| 4,359,404 A | 11/1982 | Grey et al. | |
| 4,370,507 A | 1/1983 | Hargis et al. | |
| 4,371,619 A | 2/1983 | Schwartz et al. | |
| 4,379,028 A | 4/1983 | Berg et al. | |
| 4,405,717 A | 9/1983 | Urbas | |
| 4,421,939 A | 12/1983 | Kiff et al. | |
| 4,431,838 A | 2/1984 | Feldman et al. | |
| 4,435,595 A | 3/1984 | Agreda et al. | |
| 4,444,881 A | 4/1984 | Urbas | |
| 4,454,358 A | 6/1984 | Kummer et al. | |
| 4,497,967 A | 2/1985 | Wan | |
| 4,506,012 A | 3/1985 | Reed | |
| 4,513,084 A | 4/1985 | Keller, Jr. et al. | |
| 4,517,391 A | 5/1985 | Ludwig et al. | |
| 4,568,644 A | 2/1986 | Wang et al. | |
| 4,569,726 A | 2/1986 | Berg et al. | |
| 4,636,467 A | 1/1987 | Chynoweth | |
| 4,649,112 A | 3/1987 | Datta et al. | |
| 4,652,526 A | 3/1987 | Hsu | |
| 4,687,668 A | 8/1987 | Ghommidh et al. | |
| 4,690,912 A | 9/1987 | Paulik et al. | |
| 4,698,303 A | 10/1987 | Bailey et al. | |
| 4,771,001 A | 9/1988 | Bailey et al. | |
| 4,808,526 A | 2/1989 | Lawford | |
| 4,830,963 A | 5/1989 | Brumm et al. | |
| 4,876,196 A | 10/1989 | Salzbrunn et al. | |
| 4,935,360 A | 6/1990 | Klemps et al. | |
| 4,939,294 A | 7/1990 | Agreda et al. | |
| 4,980,164 A | 12/1990 | Manfredi et al. | |
| 5,028,539 A | 7/1991 | Ingram et al. | |
| 5,068,188 A | 11/1991 | Wise et al. | |
| 5,071,754 A | 12/1991 | Walkup et al. | |
| 5,093,121 A | 3/1992 | Kvanta et al. | |
| 5,162,214 A | 11/1992 | Hubred | |
| 5,173,429 A | 12/1992 | Gaddy et al. | |
| 5,182,199 A | 1/1993 | Hartley | |
| 5,210,296 A | 5/1993 | Cockrem et al. | |
| 5,231,017 A | 7/1993 | Lantero et al. | |
| 5,254,465 A | 10/1993 | Wise | |
| 5,308,619 A | 5/1994 | Schmeider et al. | |
| 5,316,928 A | 5/1994 | Flickinger et al. | |
| 5,453,365 A | 9/1995 | Sterzel et al. | |
| 5,510,526 A | 4/1996 | Baniel et al. | |
| 5,591,877 A | 1/1997 | Obermeier et al. | |
| 5,599,976 A | 2/1997 | Scates et al. | |
| 5,681,728 A | 10/1997 | Miao | |
| 5,693,296 A | 12/1997 | Holtzapple et al. | |
| 5,750,732 A | 5/1998 | Verser et al. | |
| 5,753,474 A | 5/1998 | Ramey et al. | |
| 5,773,653 A | 6/1998 | Baniel | |
| 5,780,276 A | 7/1998 | Baniel | |
| 5,865,898 A | 2/1999 | Holtzapple et al. | |
| 5,874,263 A | 2/1999 | Holtzapple et al. | |
| 5,892,102 A | 4/1999 | Mikami et al. | |
| 5,969,189 A | 10/1999 | Holtzapple et al. | |
| 5,986,133 A | 11/1999 | Holtzapple et al. | |
| 6,043,392 A | 3/2000 | Holtzapple et al. | |
| 6,368,819 B1 | 4/2002 | Gaddy et al. | |
| 6,509,180 B1 * | 1/2003 | Verser et al. | 435/161 |
| 6,703,227 B2 | 3/2004 | Jakel et al. | |
| 6,740,508 B2 | 5/2004 | Ulrich et al. | |
| 6,927,048 B2 | 8/2005 | Verser et al. | |
| 7,074,603 B2 | 7/2006 | Verser et al. | |
| 2004/0168960 A1 | 9/2004 | Holtzapple et al. | |
| 2004/0171136 A1 | 9/2004 | Holtzapple et al. | |
| 2006/0019360 A1 | 1/2006 | Verser et al. | |
| 2006/0024801 A1 | 2/2006 | Holtzapple et al. | |
| 2006/0127999 A1 | 6/2006 | Verser et al. | |
| 2006/0188980 A1 | 8/2006 | Holtzapple et al. | |

FOREIGN PATENT DOCUMENTS

| | | |
|---|---|---|
| WO | WO 82/03854 | 11/1982 |
| WO | WO 83/03409 | 10/1983 |
| WO | WO 00/53791 | 9/2000 |

OTHER PUBLICATIONS

Busche, Robert M., *Recovering Chemical Products from Dilute Fermentation Broths*, Biotechnology and Bioengineering Symp. No. 13, 597-615 (1983).

Filachione et al., *Preparation of Esters by Reaction of Ammonium Salts with Alcohols*, 5265-5267 (Nov. 1951) [Presented in part at the 116$^{th}$ A.C.S. Meeting held in Atlantic City, N.J., Sep. 1949, and also at the Miniature meeting of the Philadelphia Section of the American Chemical Society held in Philadelphia, PA., in Jan. 1949.].

Husson et al., *Regeneration of Lactic and Succinic Acid-Laden Basic Sorbents by Leaching with a Volatile Base in an Organic Solvent*, Ind. Eng. Chem. Res. 37:2996-3005 (1998).

Parekh et al., *Acetate Production from Glucose by Clostridium Thermoaceticum*, Process Biochemistry International, 117-121 (Aug. 1990).

Zhicai et al., *Esterification—Distillation of Butanol and Acetic Acid*, Chemical Engineering Science, 53(11):2081-2088 (1998).

Reisinger et al., *Extraction and Sorption of Acetic Acid at pH above $pK_a$ to Form Calcium Magnesium Acetate*, Ind. Eng. Chem. Res., 34:845-852 (1995).

Ricker et al., *Solvent Properties of Organic Bases for Extraction of Acetic Acid From Water*, J. Separ. Proc. Technol., 1:36-41 (1979).

Ricker et al., *Solvent Extraction With Amines for Recovery of Acetic Acid From Dilute Aqueous Industrial Streams*, J. Separ. Proc. Technol., 1(2):23-30 (1980).

Schwartz et al., *Acetic Acid Production by Clostridium Thermoaceticum in pH-Controlled Batch Fermentations at Acidic pH*; Applied and Environmental Microbiology, 1385-1392 (Jun. 1982).

Tamada et al., *Extraction of Carboxylic Acids with Amine Extractants. 3. Effect of Temperature, Water Coextraction, and Process Considerations*, Ind. Eng. Chem. Res. 29:1333-1338 (1990).

Wardell et al., *Solvent Equilibria for Extraction of Carboxylic Acids from Water*, Journal of Chemical and Engineering Data, 23(2):144-148 (1978).

"A Renewed Boost for Ethanol", Chemical Engineering, Feb. 1999, p. 35-39.

Agreda et al., Chem. Eng. Prog., "High Purity Methyl Acetate by Reactive Distillation", pp. 40-46, Feb. 1990.

Balasubramanian, N., Kim, J.S., Lee, Y.Y., "Fermentation of Xylose into Acetic Acid by *Clostridium thermoaceticum*", Appl Biochem and Biotech, vol. 91-93, p. 367-376, 2001.

Ben-Bassat et al., "Ethanol production by thermophilic bacteria: metabolic control of end product formation in *Thermoanaerobium brockii*", J Bacteriol Apr. 1981, 146:1, p. 192-9 (Abstract only).

Bock et al., Biotechnol. Appl. Biochem., "Development of a Low-Cost, Industrially Suitable Medium for the Production of Acetic Acid From *Clostridium thermoaceticum*", vol. 25, pp. 117-125 (1997).

Borden, J.R., Lee, Y.Y., Yoon, H.H., "Simultaneous Saccharification and Fermentation of Cellulosic Biomass to Acetic Acid", Appl Biochem and Biotech, vol. 84-86, p. 963-970, 2000.

Brownell, J., Nakas, J., "Bioconversion of Acid-Hydrolyzed Poplar Hemicellulose to Acetic Acid by *Clostridium thermoaceticum*", J. Ind. Microbiol. vol. 7, p. 1-6, 1991.

Chang, V.S., Holtzapple, M.T., "Fundamental Factors Affecting Biomass Enzymatic Reactivity", Appl. Biochem. and Biotech., vol. 84-86, p. 5-37, 2000.

Daniel, S.L., Keith, E.S., Yang, H., Lin, Y.S., Drake, H.L., Utilization of Methoxylated Aromatic Compounds by the Acetogen *Clostridium thermoaceticum*: Expression and.

Grohmann et al., Process Biochem., "Saccharification of Corn Fibre by Combined Treatment with Dilute Sulphuric Acid and Enzymes", vol. 32, No. 5, pp. 405-415 (1997).

Gulati et al. "Assessment of Ethanol Production Options For Corn Products", Bioresource Technology 58, 1996, p. 253-264.

Hull, S.R., Yang, B.Y., Venzke, D., Kulhavy, K., Montgomery, R., "Composition of Corn Steep Water During Steeping", J. Agric. Food Chem., vol. 44, p. 1857-1863, 1996.

Karnholz, A., Kusel, K., Grossner, A., Schramm, A., Drake, H.L., "Tolerance and Metabolic Response of Acetogenic Bacterial Toward Oxygen", Applied and Environmental Microbiology, vol. 68, No. 2, p. 1005-1009, 2002.

Leathers et al., "Saccharification of Corn Fiber Using Enzymes from Aureobasidium sp. Strain NRRL Y-2311-1", Applied Biochemistry and Biotechnology, vol. 59, 1996, p. 337-347.

Liden et al., Two amperometric biosensors as liquid chromatographic detectors for on-line monitoring of carbohydrate consumption and ethanol production in bioprocesses, 8th International Conference on Solid-State Sensors and Actuators, and Eurosensors IX, Stockholm, Sweden, Jun. 1996, vol. 1:474-477.

Luo et al., "Kinetics of Simultaneous Saccharification and Lactic Acid Fermentation Processes", Biotechnol. Prog. 1997, 13, 762-767.

Lovitt et al., "Ethanol production by thermophilic bacteria: biochemical basis for ethanol and hydrogen tolerance in *Clostridium thermohydrosulfuricum*" J Bacteriol Jun. 1988, 170:6, p. 2809-15 (Abstract only).

Luedeking et al., J. Biochem. Microbiol. Tech. Eng., "A Kinetic Study of the Lactic Acid Fermentation; Batch Process at Controlled PH", Robert Luedeking & Edgar L. Piret, vol. 1, No. 1, pp. 393-412, 1959.

Lundie (Jr.), L.L., Drake, H.L, "Development of a Minimally Defined Medium for the Acetogen *Clostridium thermoaceticum*", J. of Bacteriology, vol. 159, No. 2, p. 700-703, 1984.

Matar et al. "Chemistry of Petrochemical Processes", Gulf Publishing Company, 1994, cover, contents, p. 162-163.

McCoy "Biomass Ethanol Inches Forward", C&EN, Dec. 7, 1998, p. 29-32.

Richert et al., "Thermophilic Fermentation to Make Ethanol from Carbohydrate Byproducts", Genetic Engineering News, Oct. 1, 1998, 1 page.

Savage, M.D., Drake, H.L., "Adaptation of the Acetogen *Clostridium thermoautotropicum* to Minimal Medium", Journal of Bacteriology, vol. 165, No. 1, p. 315-318, 1986.

Schwartz, R.D., Keller Jr., F.A., "Isolation of a Strain of *Clostridium thermoaceticum* Capable of Growth and Acetic Acid Production at pH 4.5", Applied and Environmental Microbiology, vol. 43, No. 1, p. 117-123, 1982.

Tang et al., Appl. Microbiol. Biotechnol., "Acetic Acid Production From Whey Lactose by the Co-Culture of *Sterpococcus lactis* and *Clostridium formicoaceticum*", 28:138-143 (1988).

Wang et al., Biochem. Eng. Renewable Sources, "A Novel Route to the Production of Acetic Acid by Fermentation", No. 181, vol. 74, pp. 105-110 (1978).

Witjitra, K., Shah, M.M., Cheryan, M., "Effect of Nutrient Sources on Growth and Acetate Production by *Clostridium thermoaceticum*", Enzyme and Microbial Technology, vol. 19, p. 322-327, 1996.

Xu et al., Canadian J. Chem. Eng., "Kinetics of Acetic Acid Esterification Over Ion Exchange Catalysts", vol. 74, pp. 493-500, Aug. 1996.

Yang et al., Biotechnol. Bioeng., "Kinetics and Mathematical Modeling of Homoacetic Fermentation of Lactate by *Clostridium formicoaceticum*", vol. 32, pp. 797-802 (1988).

Zeikus et al., "Thermophilic Ethanol Fermentations", Basic Life Sci, 1981, vol. 18, pp. 441-61 (Abstract only).

International Search Report for International (PCT) Patent Application No. PCT/US00/06498, mailed Aug. 14, 2000.

International Preliminary Examination Report for International (PCT) Patent Application No. PCT/US00/06498, mailed Nov. 6, 2000.

Examiner's First Report for Australian Patent Application No. 38794/00, mailed Jul. 30, 2002.

Examiner's Report No. 2 for Australian Patent Application No. 38794/00, mailed Dec. 4, 2002.

Examiner's Report No. 3 for Australian Patent Application No. 38794/00, mailed Apr. 24, 2003.

Examiner's First Report for Australian Patent Application No. 2004200701, mailed Oct. 11, 2005.

Examiner's Report No. 2 for Australian Patent Application No. 2004200701, mailed Dec. 13, 2006.

Examiner's Report No. 3 for Australian Patent Application No. 2004200701, mailed Mar. 16, 2007.

First Office Action for Chinese Patent Application No. 00804895.9, issued Jul. 25, 2003.

Second Office Action for Chinese Patent Application No. 00804895.9.

Supplementary Partial European Search Report for European Patent Application No. 00917888, mailed Feb. 23, 2004.

Supplementary Partial European Search Report for European Patent Application No. 00917888, mailed Nov. 20, 2006.

Examination Report for European Patent Application No. 00917888, mailed Nov. 23, 2006.

European Search Report for European Patent Application No. 07008768, mailed Jul. 3, 2007.

Examination Report for New Zealand Patent Application No. 514253, mailed May 7, 2002.

Examination Report for New Zealand Patent Application No. 514253, mailed Jan. 23, 2003.

Search Report for International (PCT) Patent Application No. PCT/US2005/003434, mailed Apr. 26, 2005.

Written Opinion for International (PCT) Patent Application No. PCT/US2005/003434, mailed Apr. 26, 2005.

International Preliminary Examination Report for International (PCT) Patent Application No. PCT/US2005/003434, mailed Aug. 10, 2006.

U.S. Appl. No. 12/051,668, filed Mar. 19, 2008, Verser et al.

Miller, Richard W. et al: "Extraction of Lactic Acid from a Calcium Lactate Solution Using Amine-Containing Solvents and Carbon Dioxide Gas. 1. Experimental Procedures" Industrial & Engineering Chemistry Research , 35(4), 1156-62, 1996.

Xin et al. "Recovery of acetic acid from waste water", Chemical Engineering (China), vol. 24, No. 5, pp. 41-44, (including translated abstract), Oct. 25, 1996.

Examination Report for European Patent Application No. 07008768, mailed Feb. 27, 2008.

Supplementary European Search Report for European Patent Application No. EP 05712766, mailed Jan. 11, 2008.

Translation of Office Action for Chinese Patent Application No. 200580008137.0, mailed Jul. 11, 2008.

* cited by examiner (25 °C, Mass Fraction Basis)

RECOVERY OF ORGANIC ACIDS

CROSS-REFERENCE TO RELATED APPLICATIONS

The present application claims priority from U.S. Provisional Patent Application Ser. No. 60/540,606, filed Jan. 29, 2004, and from U.S. Provisional Patent Application Ser. No. 60/550,659, filed Mar. 5, 2004, and from U.S. Provisional Patent Application Ser. No. 60/570,134, filed May 10, 2004. All three provisional applications are incorporated herein by reference in their entirety.

GOVERNMENT SUPPORT

This invention was supported in part with funding provided by Grant No. DE-FG36-03GO13010, awarded by the United States Department of Energy. The government may have certain rights to this invention.

FIELD OF THE INVENTION

The present invention is related to methods for recovery of organic acids from dilute salt solutions, such as fermentation broths.

BACKGROUND OF THE INVENTION

Organic acids are valuable products in their own right as food and feed ingredients, for example, or as intermediates. Organic acids can be converted chemically to alcohols, which can subsequently be converted to olefins. Such a process could be envisioned as the basis for a biorefinery to convert biomass resources into a range of products for the energy and chemical industries. Organic acids can be produced by fermentation at very high carbon yield from a wide range of biomass resources.

Many valuable carboxylic acids such as acetic, lactic and propionic acids can be produced by fermentation. Holten, *Lactic Acid: Properties and Chemistry of Lactic Acid and Derivatives*, Verlag Chemie, 1971; Benninga, (1990), *A History of Lactic Acid Making: A Chapter in the History of Biotechnology*, Kluwer Academic Publishers, London; Partin, L., Heise, W. (1993), in *Acetic Acid and Its Derivatives*, Agreda, V., Zoeller, J., ed., Marcel Dekker, New York, pp. 3-13; Playne, 1985 Propionic and butyric acids pp. 731-759, In M. Moo-Young (ed.) *Comprehensive Biotechnology*, vol. 3, Pergamon, Oxford. However, today almost all carboxylic acids are produced from petrochemicals.

One reason why fermentation routes have failed to compete is that the micro-organisms used to produce these acids are inhibited by low pH. In order to achieve high yields, the pH of the fermentation step has to be kept near neutral by the addition of a base such as ammonia, sodium hydroxide or calcium hydroxide. In addition, even at neutral pH, the acids generally inhibit the growth of the organisms used in the fermentation and limit the broth to low concentrations of the acid salt. Thus, the fermentation routes typically produce a dilute aqueous solution of the organic acid salt rather than the organic acid in its protonated form. The salts are highly water-soluble, have a negligible vapor pressure and the carbonyl group is unreactive. These properties make recovery of the salt difficult since distillation, extraction, crystallization and other common industrial separation methods for large-scale production are either technically or economically infeasible.

One way to ease the recovery of organic acid salts is to add a mineral acid to lower the pH of the broth, thereby converting the organic acid into its protonated form. In its protonated form, the organic acid can be more easily recovered by known means such as distillation, extraction or reactive separation processes. Direct acidification with a mineral acid is usually regarded as a troublesome option for recovery of organic acid salts because a salt byproduct is inevitably formed. This byproduct is often of very low value. For example, gypsum is historically the salt co-produced in lactic acid production. (Holten, 1971, Benninga, 1990)

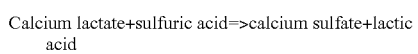

Markets either have to be found or an environmentally responsible disposal method has to be identified. Because of these limitations, much research has gone into alternative methods to recover organic acids.

Recovery of fermentation-derived acetate has been summarized by Busche (Busche, R. M., "Recovering Chemical Products from Dilute Fermentation Broths", Biotechnology and Bioengineering Symp. No. 13, p. 597-615, 1983 and co-workers at Du Pont (Busche et al., "Recovery of Acetic Acid from Dilute Acetate Solution", Biotechnology and Bioengineering Symp. No. 12, p. 249-262, 1982) and by Partin and Heise, 1993.

Once the organic acid has been produced in solution in its protonated form by direct acidification, various means can be used for its recovery from the broth (Othmer, "Acetic Acid Recovery Methods", Chemical Engineering Progress, Vol. 54, No. 7, July, 1958, Baniel et al., U.S. Pat. No. 4,275,234). For example, solvent extraction of organic acids from dilute solution has been studied in detail. (King, et al., "Solvent Equilibrium for Extraction of Carboxylic Acids from Water", Journal of Chemical and Engineering Data, Vol. 23, No. 2, 1978). Baniel (U.S. Pat. No. 5,780,276) also mentions the use of enhancers in extraction of amines including small amounts of alcohols. However, Baniel (U.S. Pat. No. 5,780,276) provides processes for the recovery of the small amount (10%) of enhancer alcohol and does not suggest its reaction with the organic acid.

Busche (Busche, 1983) discusses general concepts that apply for recovery of organic chemicals present in dilute fermentation broths. He concludes that distillation is preferred for recovery of species with boiling points lower than water (e.g. ethanol) since the product is distilled overhead. If the species has a boiling point higher than water (e.g. acetic acid, propionic acid, lactic acid), then distillation is not preferred since the energy required to boil water and remove it as the overhead product is excessive. He also surveys other means for recovery of high boilers such as extraction, crystallization, evaporation and electrodialysis.

Although not considered by Busche (Busche, 1983), reactive distillation converts a carboxylic acid (a high boiler) into volatile ester (a low boiler), thus sidestepping the energy penalty associated with boiling water. (Xu and Chuang, "Kinetics of Acetic Acid Esterification over Ion Exchange Catalysts", Can. J. Chem. Eng., pp. 493-500, Vol. 74, 1996, Scates et al, "Recovery of Acetic Acid from Dilute Aqueous Streams Formed During a Carbonylation Process", U.S. Pat. No. 5,599,976, Feb. 4, 1997).

Many advances have been made in membrane processes during the last two decades. Crossflow microfilters and ultrafilters are routinely used to clarify broths by removing cell mass and insoluble materials. Further clarification by nanofiltration removes high molecular weight soluble impurities such as proteins and residual carbohydrates, and provides the additional benefit of concentrating the organic acid salt prior to downstream recovery. Bipolar electrodialysis can be used to acidify the broth. A patent assigned to Chronopol, Inc. (Miao, "Method and Apparatus for the Recovery and Purification of Organic Acids", U.S. Pat. No. 5,681,728, Oct. 28, 1997) gives an example of how to sequence the various membrane units to recover and acidify lactic acid from a fermentation broth. Economics for membrane-based processes are favorable today for high value, low volume products. Scale-up of capital cost is nearly linear, so membrane systems are not always competitive for large-scale production of bio-commodities unless high flux is achieved. This is especially true when considering the more complex membrane processes such as bipolar electrodialysis.

Work at DuPont (Yates, "Removal and Concentration of Lower Molecular Weight Organic Acids From Dilute Solutions", U.S. Pat. No. 4,282,323, Aug. 4, 1981 and Busche et. al., 1982) discusses the use of carbon dioxide as an acidulant to convert fermentation-derived acetate salts into acetic acid and subsequent solvent extraction. Researchers at Cargill (Baniel et. al., "Lactic Acid Production, Separation, and/or Recovery Process", U.S. Pat. No. 5,510,526, Apr. 23, 1996) have investigated a related method for recovery of lactate by acidification with $CO_2$ and concurrent extraction with an amine. However, this reaction requires high pressure and produces multiple phases (4) at the same point in the process.

Researchers at CPC International (Urbas, "Recovery of Acetic Acid from a Fermentation Broth", U.S. Pat. No. 4,405,717, Sep. 20, 1983 and Urbas, "Recovery of Organic Acids from a Fermentation Broth", U.S. Pat. No. 4,444,881, Apr. 24, 1984) also discuss the use of carbon dioxide as an acidulant. Tributylamine (TBA) is normally immiscible with water, but the tributyl amine: acetic acid complex (TBA:HAc) is water soluble. When a dilute aqueous solution of calcium acetate at near neutral pH is mixed with TBA, and then carbon dioxide is bubbled through the mixture, the following reaction occurs at or near ambient temperatures:

Ca(Ac)$_2$+H$_2$O+CO$_2$+2 TBA=>2 TBA:HAc+CaCO$_3$

Use of a stoichiometric amount of TBA produces a single aqueous liquid phase containing the tributyl amine:acetic acid complex. The reaction is driven to the right since calcium carbonate precipitates upon formation. The amine must be suitably chosen such that its acid/amine complex is completely water soluble. Urbas (Urbas, U.S. Pat. No. 4,405,717) also mentions dicyclohexyl methyl amine.

In one embodiment of the Urbas process, the aqueous amine complex is extracted into an organic solvent, the solvent is stripped off, and the complex is thermally split apart giving the acetic acid product and regenerating both the solvent and amine for recycle. The amine used in the extraction process must be extractable. Urbas shows that amine:acid complexes that are too water soluble cannot be extracted including trimethyl and triethyl amine acid complexes. For extraction, Urbas teaches the use of low boiling, non-reactive solvents that do not azeotrope with acetic acid, with preference given to chloroform. These are severe limitations on solvent selection. Furthermore, use of chlorinated solvents, such as chloroform, would be problematic at industrial scale.

In another embodiment of the Urbas process, the amine acid complex is concentrated by the removal of the water and then thermally cracked to generate the free acid and regenerate the amine. In general, there have been two approaches to recovery of acid/amine complexes, back extraction into water or an aqueous base, or evaporation of the water and then recovery of the acid. However, water removal is extremely energy intensive as outlined previously.

The thermal regeneration reaction has been found by the present inventors to be difficult in practice, leading to a viscous intractable residue and low yield of acetic acid.

In the Urbas process, the calcium carbonate can be recycled for use as a base for neutralization of the fermentation step. No other salt byproduct is created, and this feature is a significant advantage for this route. The use of calcium carbonate as a base in an organic acid fermentation produces $CO_2$ which can be utilized in the reaction step to form the acid/amine complex and the calcium carbonate, so there is not net production of $CO_2$.

Urbas teaches away from the use of solvents which can form esters with the organic acid. However, the present inventors have found that an ester may be a valuable intermediate or product. For example, the use of an alcohol solvent that potentially forms an ester with the acid can be integrated into an indirect ethanol process for example as disclosed in U.S. Pat. No. 6,509,180 (Verser and Eggeman, to ZeaChem) incorporated herein in its entirety by reference. The ZeaChem process describes the production of ethanol by production of acetic acid, esterification of the acid with an alcohol and subsequent hydrogenation of the ester.

The production of esters of organic acids is well known. Esters have been used as an intermediate in the recovery and purification of organic acids. Methods such as reactive distillation as mentioned previously can be used if the acid is in the protonated form, i.e., the free acid. (Benninga 1990, Scates) Various catalysts have been explored to facilitate this reaction including cationic ion exchange resins, strong mineral acids such as sulfuric, hydrochloric and nitric, and strong organic acids such as methane sulfonic acid or toluene sulfonic acid. (Xu and Chuang, 1996, Filachione et al., "Production of Esters", U.S. Pat. No. 2,565,487, Aug. 28, 1951)

Since esterification is an equilibrium reaction, the reverse reaction of hydrolysis occurs at the same time as the forward reaction. In most processes either water, or the product ester, are removed continuously during the reaction to drive the reaction in the desired forward direction.

Direct esterification of acid/amine complexes have been reported by several groups (Filachione, 1951, Tung et al, "Sorption and Extraction of Lactic and Succinic Acids at pH>pKa, 2. Regeneration and Process Considerations", Industrial and Engineering Chemistry, Vol. 33, pgs. 3224-3229, 1994, Sterzel et al, "Preparation of Lactates, U.S. Pat. No. 5,453,365, Sep. 26, 1995). Each of these references reports the esterification of the concentrated complex in which the bulk of the water is removed by evaporation or distillation overhead. Thus, these processes suffer from the energy penalty of vaporizing the water.

The hydrogenation or hydrogenolysis of esters to produce an alcohol from the organic acid moiety and to regenerate the alcohol of the ester is well known. McKee, WO 00/53791 Alcohols produced by hydrogenation of esters can also be converted to an olefin derived from the organic acid moiety. The dehydration of alcohols to olefins has been described (Tsao et al., "Dehydrate Ethanol to Ethylene", Hydrocarbon Processing, 57(2), p. 133-136, February 1978). The process has been practiced at the commercial scale for ethanol dehydration to ethylene. The process is carried out in a fluidized bed with a phosphoric acid catalyst on an inert support.

Similarly, propionic acid can be produced by fermentation, converted to propanol by hydrogenation of a suitable ester and then dehydrated to propylene. (Playne, 1985)

In addition, various esters can be interconverted by trans-esterification, by reacting one ester with an excess of a second alcohol to form the ester of the second alcohol. Various processes are known in the art for transesterification such as reactive distillation.

Esters may also be hydrolyzed to regenerate the organic acid and the alcohol. Lactic acid has been recovered and purified by esterification with methanol and subsequent hydrolysis. (Benninga, 1990)

SUMMARY OF THE INVENTION

One embodiment of the present invention is a method for recovery of an organic acid from a dilute salt solution that includes an organic acid salt. The cation of the salt forms an insoluble carbonate salt. The method includes introducing a tertiary amine and carbon dioxide to the dilute salt solution to form an acid/amine complex, as well as the insoluble carbonate salt. A water immiscible solvent is introduced to the dilute salt solution to form a reaction phase that includes the acid/amine complex and the water immiscible solvent. The method further includes continuously drying the reaction phase and forming a product between the acid and the water immiscible solvent.

A further embodiment of the present invention is a method for recovery of an organic acid from a dilute salt solution that includes a calcium salt of an organic acid. The method includes introducing a tertiary amine and carbon dioxide to the dilute salt solution, forming an acid/amine complex and calcium carbonate. The dilute salt solution is mixed with a water immiscible alcohol having a distribution coefficient of at least about 0.5, and the acid/amine complex is extracted into the water immiscible alcohol. The method further includes continuously drying the water immiscible alcohol and forming an ester from the acid and the alcohol. In this manner, a mixture comprising the ester, residual water immiscible alcohol, and the tertiary amine is produced.

A still further embodiment of the present invention is a method for recovery of an organic acid selected from acetic acid, lactic acid and propionic acid from a fermentation broth that includes a calcium salt of the organic acid. The method includes introducing carbon dioxide and either tributylamine or dicyclohexyl methyl amine to the dilute salt solution to form an acid/amine complex and calcium carbonate. The dilute salt solution is mixed with a water immiscible alcohol that is selected from n-octanol, n-hexanol, n-pentanol, or n-butanol. In this manner, the acid/amine complex is extracted into the water immiscible alcohol. The method further includes continuously drying the alcohol and forming an ester from the acid and the alcohol to produce a mixture that includes the ester, the alcohol and the tertiary amine. The method further includes separating the ester, the tertiary amine, and the alcohol. The separated tertiary amine is used as the tertiary amine for introduction to the dilute salt solution to form the acid/amine complex. The separated water immiscible alcohol is used as the alcohol to be mixed with the dilute salt solution for extraction of the acid/amine complex. The separated ester is treated for further recovery by either hydrogenating the ester to form an alcohol of the acid and regenerate the solvent alcohol, transesterifying the ester with a second alcohol to form a second ester, or hydrolyzing the ester to form the acid and regenerate the solvent alcohol.

A still further embodiment of the present invention is a method for recovery of an organic acid from an acid/amine complex in an aqueous solution. The method includes introducing a water immiscible solvent to the aqueous solution to form a reaction phase and an aqueous phase. The reaction phase includes the acid/amine complex and the water immiscible solvent. The method further includes continuously drying the reaction phase and forming a product of the acid and the water immiscible solvent.

In various embodiments of the invention, the water immiscible solvent can be an alcohol, and in that instance, the acid/solvent product can be an ester. The alcohol can be selected from the group of n-octanol, n-hexanol, n-pentanol, and n-butanol. The water immiscible solvent can also be a mixed solvent that includes a solvent reactive with the acid portion of the acid/amine complex and a solvent that is inert with the acid portion of the acid/amine complex. In various other embodiments, the water immiscible solvent can have a distribution coefficient of at least about 0.5, at least about 0.75, or at least about 1. In still further embodiments, the water immiscible solvent can have a selectivity value of at least about 8, at least about 15, or at least about 20.

The tertiary amine, in various embodiments, can be either tributylamine or dicyclohexyl methyl amine.

The organic acid of the invention can be selected from acetic acid, lactic acid, propionic acid, butyric acid, succinic acid, citric acid, 3-hydroxypropionic acid, glycolic acid, or formic acid.

The step of continuously drying a reaction phase in various embodiments of the present invention can include either removing water as an azeoptrope with the solvent by azeotropic distillation or removing water by contacting the reaction phase with a water adsorbent.

The step of forming the acid/solvent product can comprise forming an ester between the acid and an alcohol solvent by the production of water. Further, the step of forming the acid/solvent product can include adding a catalyst to the solvent. The catalyst can be a strong acid catalyst, such as acid catalysts having a pKa less than the organic acid and solid catalysts. The catalyst can be selected from sulfuric acid, hydrochloric acid and methane sulfonic acid.

In further embodiments of the invention, the method can include separating the acid/solvent product, the tertiary amine, and the solvent from the reaction phase. The separated tertiary amine can be used as the amine which is introduced to the dilute salt solution to form the acid/amine complex. Further, the separated solvent can be used as the water immiscible solvent to be added to the dilute salt solution. The step of separating can be conducted by distilling the acid/solvent product from the tertiary amine and the solvent. Further, the step of separating can include distilling the solvent from the tertiary amine.

When the acid/solvent product is an ester formed between the acid and an alcohol, the method can further include hydrogenating the ester to form an alcohol of the acid and regenerate the solvent alcohol. In this embodiment, the alcohol of the acid can be dehydrated to form an olefin. Further, in this embodiment, the regenerated solvent can be used as the solvent to be introduced to the dilute salt solution. In a further embodiment, an acid/solvent ester product can be transesterified with a second alcohol to form a second ester. Still further, an acid/solvent ester product can be hydrolyzed to form an acid and regenerate the solvent alcohol, which can be recycled for introduction into a dilute salt solution.

DETAILED DESCRIPTION OF THE INVENTION

Figure 1:
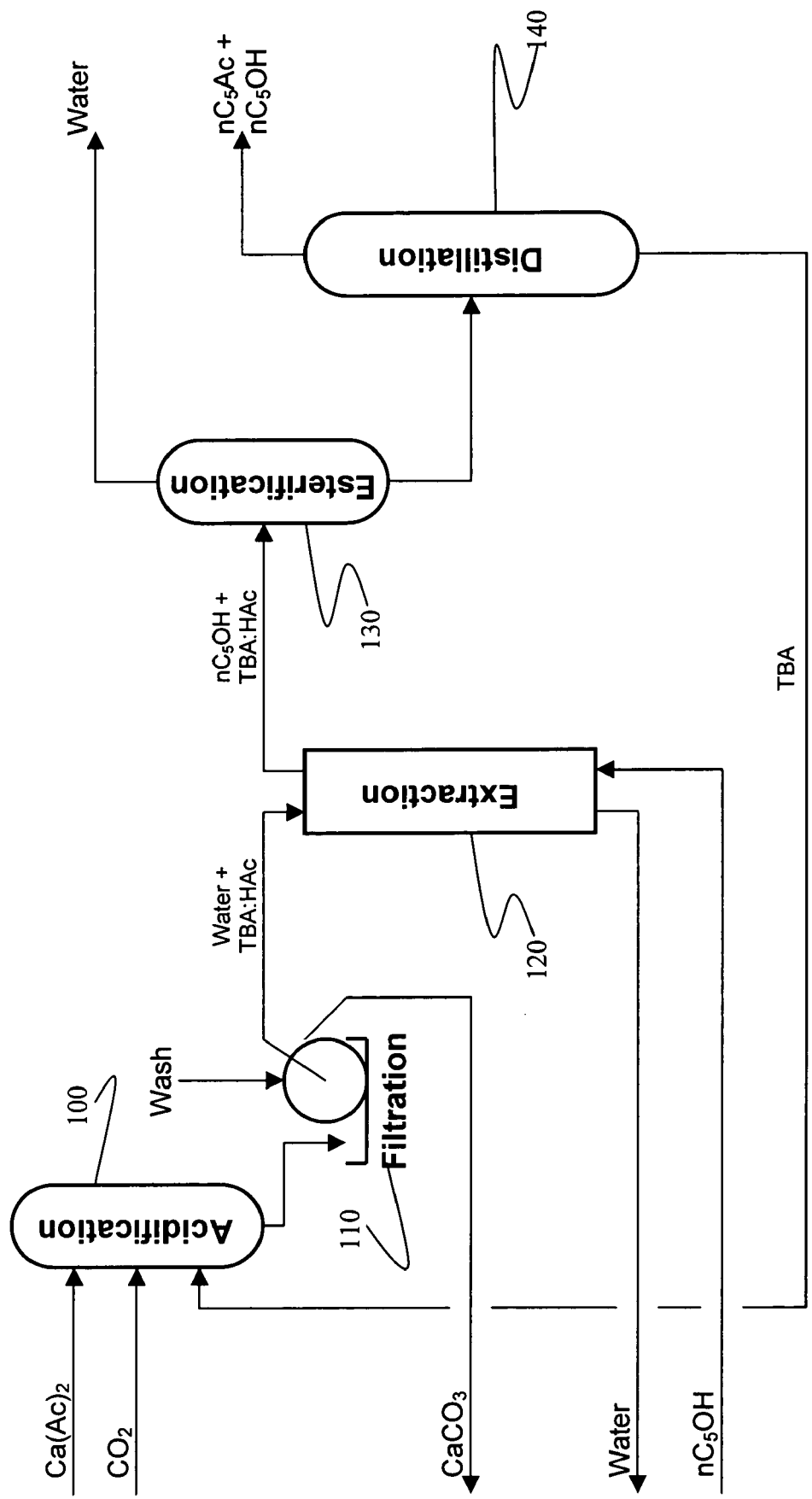
FIG. 1 is a block flow diagram of an embodiment of the present invention.

In one embodiment of the present invention, a method for recovery of an organic acid from a dilute salt solution is provided. The dilute salt solution includes an organic acid salt, the cation of which forms an insoluble carbonate salt. The process includes introducing a tertiary amine and $CO_2$ to the salt solution to form an acid/amine complex and the insoluble carbonate salt. The process further includes introducing a water immiscible solvent to the dilute solution to form a reaction phase that includes the acid/amine complex in the water immiscible solvent. The reaction phase is continuously dried. The method further includes forming a product of the acid and the water immiscible solvent.

This embodiment of the present invention is particularly suitable for use with organic acids in dilute salt solutions that are produced by fermentation. For example, such organic acids can include acetic acid, lactic acid, propionic acid, butyric acid, succinic acid, citric acid, 3-hydroxypropionic acid, glycolic acid, formic acid, and others, and preferably, includes acetic acid, lactic acid, and propionic acid. The organic acid salt in this embodiment comprises a cation that forms an insoluble carbonate salt. For example, calcium carbonate is insoluble. Other suitable cations in addition to Ca include Zn, Ba, and Mg.

The step of introducing a tertiary amine and $CO_2$ to the dilute salt solution is typically conducted at near neutral pH while the solution is mixed with the tertiary amine with the $CO_2$ being bubbled through the mixture. In this manner, the organic acid salt reacts with water, $CO_2$ and the tertiary amine to form an acid/amine complex and the insoluble carbonate salt. The carbonate salt will fall out of the solution, thereby driving the reaction in the direction of forming the acid/amine complex, essentially to completion. A significant advantage of the present invention is that this reaction can be conducted under ambient conditions of temperature and pressure and at near neutral pH, such as the pH of a fermentation broth.

The insoluble carbonate salt, such as calcium carbonate, can be easily recovered by conventional solid-liquid separation. In one embodiment, this salt can be used as a base in an organic acid fermentation for pH control during an initial production of an organic acid. Such use of calcium carbonate during a fermentation produces $CO_2$ which can be used in various embodiments of the invention to form an acid/amine complex and insoluble carbonate salt. In this integrated process, there is not net production of $CO_2$. Thus, the step of introducing $CO_2$ to a dilute salt solution as an acidulant provides significant advantages because it overcomes the consumption of mineral acid and the issue of salt disposal in the recovery of organic acids.

Any tertiary amine, the acid/amine complex of which is soluble in a dilute salt solution, is suitable for use in this step of the process. In particular, the tertiary amine can be selected from the group consisting of tributylamine (TBA) and dicyclohexyl methyl amine.

This embodiment of the present invention further includes introducing a water immiscible solvent to the dilute salt solution to form a reaction phase that includes the acid/amine complex and the water immiscible solvent. Thus, the acid/amine complex must be at least partially soluble in the water immiscible solvent. This step in which the acid/amine complex can be extracted from a dilute aqueous solution provides the significant advantage of eliminating the high-energy cost of vaporizing the bulk of the water as a means to separate the acid/amine complex from an aqueous solution. The design of liquid-liquid extraction systems is well known to those in the art.

The water immiscible solvent can be an alcohol, such as an alcohol that is known to form esters with organic acids, and particularly, primary alcohols. More particularly, when the water immiscible solvent is an alcohol, it can be selected from n-octanol, n-hexanol, n-pentanol, and n-butanol.

The water immiscible solvent can be further characterized by its distribution coefficient, $K_D$, which is defined as the weight fraction of the acid/amine complex in the solvent divided by the weight fraction of the acid/amine complex in a second phase, such as an aqueous phase. More particularly, the water immiscible solvent can have a distribution coefficient of at least about 0.5, at least about 0.75, or at least about 1. Therefore, the use of a solvent in the extraction with a high $K_D$ is very advantageous from a process point of view because it leads to lower solvent inventory, smaller vessels and lower capital and operating cost.

The water immiscible solvent is selected so that it reacts with the acid/amine complex to form a product with the acid portion of the acid/amine complex. For example, when a water immiscible solvent is an alcohol, it reacts with the acid to form an ester. Using a solvent that reacts with the acid portion of the acid/amine complex to form a highly useful intermediate product, such as an ester, provides a high yield efficient process for recovery of the acid from the acid/amine complex.

The solvent, such as an alcohol, can be slightly soluble in water and conversely, water can be slightly soluble in the solvent. Water immiscible solvents useful in the present invention can also be characterized by their selectivities. Selectivity, defined as the distribution coefficient times the ratio of the mass fraction of water in an aqueous phase divided by the mass fraction of water in the solvent. This value is a measure of the solvent's ability to preferentially separate the acid/amine complex from water in an aqueous phase. A higher selectivity indicates that less water is brought into the water immiscible solvent, resulting in less energy being needed to remove free water in subsequent processing steps. In preferred embodiments, the water immiscible solvent has a selectivity value of at least about 8, at least about 15, or at least about 20.

In a further embodiment, the water immiscible solvent can be a mixed solvent which includes a solvent that is reactive with the acid portion of the acid/amine complex to form the acid/solvent product, as well as including a solvent that is inert with the acid portion of the acid/amine complex. For example, such mixed solvents can include as inert components toluene, xylene, aromatics, and alkanes. Such components, being relatively hydrophobic, are thought to assist by keeping water out of the water immiscible solvent, thereby improving the effective selectivity of the solvent.

In a further embodiment, the water immiscible solvent can be a mixed solvent which includes a solvent that is reactive with the acid portion of the acid/amine complex to form the acid/solvent product, as well as including another component such as an ester, that is hydrophobic. Such a component is thought to assist in the effective selectivity of the water immiscible solvent by keeping water out of the solvent phase. Such a component may also be reactive with either the acid and/or the solvent.

The reaction phase forms a separate phase from the aqueous dilute salt solution and the acid/amine complex is extracted into the reaction phase. The two phases can be separated at this point and the reaction phase further treated as described in detail below. The aqueous phase can be stripped of any residual solvent and amine by known processes such as steam stripping or carbon absorption, and the recovered solvent recycled to the process and the water discharged or recycled to the fermentation.

This embodiment of the present invention further includes continuously drying the reaction phase. As noted, the reaction phase includes the acid/amine complex and the water immiscible solvent and provides the environment for reaction between the water immiscible solvent and the acid portion of the acid/amine complex. By continuously drying the reaction phase, the presence of water which can interfere with reaction of the acid and water immiscible solvent is reduced. For example, in the instance where the water immiscible solvent is an alcohol and reacts with the acid by elimination of a water molecule, the presence of water is detrimental to the reaction proceeding to formation of an ester. By drying the reaction phase, any water initially present in the solvent is removed. Further, in this example, a water molecule is produced upon reaction of the acid and the solvent and should be removed by drying to drive the reaction in the direction of ester formation. Reference to continuously drying the reaction phase suggests making water unavailable in the reaction phase to interfere with formation of the acid/solvent product to such an extent that the product can be formed. For example, in one embodiment, the step of continuously drying the reaction phase can include removing water as an azeotrope with the solvent by azeotropic distillation. In this manner, any water initially present in the reaction phase is removed. Further, as water is generated by formation of the acid/solvent product, the water product is removed as an azeotrope by azeotropic distillation. Drying can also be conducted by the use of solid adsorbents, such as molecular sieves.

The process finally includes forming a product from the acid and the water immiscible solvent. One example of an acid/solvent product in the present invention is the formation of an ester between an acid and an alcohol solvent as discussed above. In the instance of formation of an ester between an acid and an alcohol solvent, the step of forming the product includes driving the reaction in the direction of formation of the ester by removal of water. Formation of esters can be achieved by known methods such as reactive distillation. The design of the reactive distillation is done by means known to those skilled in the art in terms of temperature, rate, residence time and other design features. The reaction may be carried out in batch or continuously.

In addition, the step of forming the product can further include addition of a catalyst to the solvent. For example, the catalyst can be a strong acid catalyst, such as a catalyst having a pKa less than the organic acid and solid acid catalysts, including both Brønsted and Lewis acids. In specific embodiments, the catalyst can be sulfuric acid, hydrochloric acid, and methane sulfonic acid.

Some of the significant advantages of the present invention are that various components of the process can be recovered and recycled for reuse in the process. Therefore, upon formation of the acid/solvent product, the process can optionally include separating the acid/solvent product, the tertiary amine, and the solvent. For example, the acid/solvent product can be distilled from the mixture, leaving the tertiary amine and the solvent, with the solvent the being distilled from the tertiary amine. In this manner, the reaction phase at the end of the process can be separated into three streams. The tertiary amine can be recycled for use in the process to be introduced with $CO_2$ to a dilute salt solution to form an acid/amine complex and the insoluble carbonate salt. Likewise, the separated solvent can be used to form the reaction phase with the acid/amine complex. Alternatively, the reaction mixture can be sent directly to hydrogenolysis after which the solvent alcohol and the product alcohol can be separated.

The acid/solvent product is a useful form in which to recover organic acids because it allows for ready formation of the acid or conversion of the acid/solvent product into other useful product forms. For example, in the instance where the acid/solvent product is an ester, the method for recovery of the organic acid can further include hydrolyzing the ester to form the acid and regenerate the solvent alcohol. In this instance, the regenerated solvent alcohol can be recycled for use as the water immiscible solvent. The conditions for conducting the step of hydrolysis of an ester are well known in the art.

Alternatively, when the acid/solvent product is an ester, the method for recovery of the organic acid can included hydrogenating the ester to form an alcohol of the acid and regenerate the solvent alcohol. Again, the regenerated solvent alcohol can be recycled for use as the water immiscible solvent. In this embodiment, the organic acid is recovered as an alcohol. The conditions for such a hydrogenation reaction are known to those of skill in the art. In a further embodiment, the alcohol of the acid can be dehydrated to form an olefin. The dehydration of alcohols to olefins has been described (Tsao et al. 1978), and the process has been practiced at the commercial scale. The process can be carried out in a fluidized bed with a phosphoric acid catalyst on an inert support. Similarly, the production of propionic acid by fermentation, conversion to propanol by hydrogenation of a suitable ester and dehydration to propylene is known. (Playne, *Comprehensive Biotech*, Chapter 37).

In a further embodiment, where the acid/solvent product is a first ester, the method can further include transesterifying the first ester with a second alcohol to form a second ester. Such transesterification reactions are known to those in the art.

With reference to FIG. 1, an embodiment of the present invention is described. In an acidification unit 100, a dilute salt solution comprising calcium acetate ($Ca(Ac)_2$) is introduced. Also introduced into the acidification unit 100 is $CO_2$ and a tertiary amine (TBA). In this unit, an acid/amine complex between the acid and TBA is formed. Also, the insoluble carbonate salt, calcium carbonate, is formed. The dilute salt solution is then filtered to remove the calcium carbonate in a filtration unit 110. The calcium carbonate is washed in the filtration unit 110 and can be used in a recycle stream as a neutralizing base in a fermentation. The TBA:HAc amine/acid complex and water is then transferred to an extraction unit 120. Also introduced to the extraction unit 120 as a water immiscible solvent is n-pentanol. The TBA:HAc amine/acid complex is extracted from the water to the n-pentanol phase. The water and solvent phases are separated, with the water being recycled. The n-pentanol phase, containing the TBA:HAc amine/acid complex is conducted to an esterification unit 130. In the esterification unit 130, the solution is continuously dried to remove any residual water. In addition, water formed by reaction of the n-pentanol with the acetic acid is taken off in the esterification unit 130. The resulting reaction mixture is then conducted to a distillation unit 140 in which the ester formed from the n-pentanol and acetic acid and residual n-pentanol are distilled off and recovered. The remaining TBA is then conducted back to the acidification unit 100 for reuse.

A particular embodiment of the present invention is a method for recovery of an organic acid from a dilute salt solution containing a calcium salt of an organic acid. This method includes introducing a tertiary amine and $CO_2$ to the dilute salt solution to form an acid/amine complex and calcium carbonate. The dilute salt solution is mixed with a water immiscible alcohol characterized by a distribution coefficient of at least about 0.5. In this manner, the acid/amine complex is extracted into the water immiscible alcohol. The method further includes continuously drying the water immiscible alcohol, and forming an ester from the acid and the water immiscible alcohol to produce a mixture comprising the ester, residual water immiscible alcohol, and the tertiary amine.

A further particular embodiment of the present invention is a method for recovery of an organic acid selected from acetic acid, lactic acid, or propionic acid from a fermentation broth having a calcium salt of the organic acid. The method includes introducing a tertiary amine and $CO_2$ to the dilute salt solution to form an acid/amine complex and calcium carbonate. The tertiary amine can be selected from tributylamine and dicyclohexyl methyl amine. The method further includes mixing the dilute salt solution with a water immiscible alcohol selected from n-octanol, n-hexanol, n-pentanol, or n-butanol. The acid/amine complex is extracted into the water immiscible alcohol, and the water immiscible alcohol is continuously dried. The method includes forming an ester from the acid and the water immiscible alcohol to produce a mixture including the ester, residual water immiscible alcohol, and the tertiary amine. The ester, the tertiary amine and the water immiscible alcohol are separated. The separated tertiary amine is recycled for introduction into the dilute salt solution, and the separated water immiscible alcohol is recycled for mixing with the dilute salt solution. The separated ester is treated by one of three processes. The first is hydrogenating the ester to form an alcohol of the acid and regenerate the solvent alcohol. The second is transesterifying the ester with a second alcohol to form a second ester. The third is hydrolyzing the ester to form the acid and regenerate the solvent alcohol.

A further particular embodiment of the present invention is a method for recovery of an organic acid from an acid/amine complex in an aqueous solution. The method includes introducing a water immiscible solvent to the aqueous solution to form a reaction phase and an aqueous phase. The reaction phase includes the acid/amine complex and the water immiscible solvent. The method further includes continuously drying the reaction phase. Finally, a product of the acid and the water immiscible solvent is formed.

The following examples are provided for the purpose of illustration and are not intended to limit the scope of the present invention.

EXAMPLES

Analytical Methods

Concentrations of acid/amine complex in both aqueous and organic solutions were determined by potentiometric titration of 10-20 ml samples diluted with 30 ml of methanol and titrated with standardized KOH in methanol following the method of Ricker, et. al., "Solvent Properties of Organic Bases for Extraction of Acetic Acid from Water", Journal of Separation Process Technology, Vol. 1, No. 1, 1979.

The water content of the organic phases was determined by Karl Fischer analysis.

Examples 1-3 illustrate the formation of an acid/amine complex and calcium carbonate using various acids and various amines. Example 4 illustrates the use of trioctyl amine which failed to react to form an acid/amine complex. Example 5 illustrates the use of a dilute salt solution, the cation of which does not form an insoluble carbonate, thereby preventing completion of formation of an acid/amine complex.

Example 1

500 ml of an aqueous calcium acetate solution (0.6 molar as acetate) was added to a 1 liter graduated cylinder and the pH was adjusted to 6.9-7.0 using acetic acid. A 5% molar excess of TBA was added, which formed a separate layer, then the solution was sparged with $CO_2$ for 30 minutes at ambient pressure. The liquid mixture became homogeneous with a single layer. A copious white precipitate of $CaCO_3$ was formed. The solution was filtered, the $CaCO_3$ cake was washed once with water, washed again with acetone, dried and then weighed. The acidification experiments were conducted four times with $CaCO_3$ yields ranging from 91.0-96.1% of theoretical. The resulting $CaCO_3$ precipitates were easy to filter and wash. A fine white powder was generated in all cases.

Example 2

The experiment of Example 1 was scaled down to about 50 mls. Side by side experiments were conducted using the acetate solution from Example 1, 0.6 molar calcium lactate, 0.6 molar calcium propionate. After gassing with $CO_2$ for 30 minutes each reaction produced the same volume of $CaCO_3$ precipitate.

Example 3

Example 2 was reproduced except that instead of gassing with $CO_2$, the reaction mixture was gassed with a mixture of nitrogen and $CO_2$ in a ratio of $N:CO_2$ of 10:1. The results were identical to those of Example 2.

Example 4

An experiment similar to Example 2 was run using only the acetate solution, but substituting trioctyl amine for the TBA. After gassing with $CO_2$ for 30 minutes there was no obvious reaction at all. There was no $CaCO_3$ precipitate and there were still two liquid layers. It is believed that trioctyl amine failed to react due to the acid/amine complex not being soluble in the calcium acetate solution.

Example 5

An experiment similar to Example 1 was run, except that a sodium acetate solution was used. No reaction appeared to have taken place. It is believed that since $NaCO_3$ is soluble and does not precipitate, that a reaction forming an acid/amine complex was not driven forward.

Example 6

This example illustrates the use of a variety of water immiscible solvents for extraction of an acetic acid/TBA complex from water.

All extraction experiments were conducted at room temperature (25° C.). For solvent screening, typically 100 g of an aqueous mixture containing 4.08 g of acetic acid (HAc) and 12.56 g of TBA, a 1:1 molar ratio, were mixed in a separatory funnel with 100 g of organic solvent. The mixture was shaken by hand and then allowed to separate. Each phase was recovered and weighed. Samples were taken and analyzed for acid/amine by the method of Ricker (Ricker et al., 1979) described above, and water by Karl Fischer.

A similar procedure was used to generate data for the liquid-liquid phase diagrams except the starting concentration of TBA:HAc was varied to generate different tie-lines.

The following table presents the data for solvent extraction of tri-butyl amine/acetate from water for a number of solvents. The solvent was mixed with an equal volume of an equimolar TBA:HAc salt in water. The sample were shaken by hand and allowed to settle. The organic phase was sampled and analyzed for acetate using the method of Ricker et al., 1979. The distribution coefficient, $K_D$, was determined. Phase volume changes were not measured so the results are only approximate, but give an indication of the merits of various solvents.

TABLE 1

Distribution Coefficients

| Solvent | Distribution Coefficient—$K_D$ |
|---|---|
| 2-octanone | 0.087 |
| Chloroform | 0.987 |
| butyl acetate | 0.082 |
| Toluene | 0.0392 |
| ethyl acetate | 0.105 |
| ethyl acetate/ethanol (2/1) | 0.293 |
| ethyl propionate/ethanol (1/1) | 0.249 |
| 1-hexanol | 0.96 |
| 1-pentanol | 1.87 |
| 1-butanol | 2.48 |

As seen in Table 1, higher alcohols give very good distribution coefficients and are potentially reactive with the acetic acid to form esters.

Example 7

This example illustrates the use of a series of higher alcohols (n-butanol, n-pentanol, n-hexanol, and n-octanol) for extraction of an acetic acid/TBA complex from water.

Primary separation was achieved quickly (<30 seconds) for all solvents included in the solvent extraction experiments. Secondary separation was also very quick for all solvents, only taking a few minutes to obtain clear solutions in both phases.

Table 2 reports the distribution coefficients and selectivities.

TABLE 2

| Solvent | Distribution Coefficient | Selectivity |
|---|---|---|
| n-Butanol | 2.40 | 8.79 |
| n-Pentanol | 1.45 | 14.77 |
| n-Hexanol | 1.13 | 19.26 |
| n-Octanol | 0.75 | 21.91 |

The example shows there is a trade-off between distribution coefficient and selectivity. Low molecular weight alcohols have more favorable distribution, but the mutual solubility of water with the low molecular weight alcohol lowers selectivity. Both n-pentanol and n-hexanol have high distribution coefficients and high selectivity.

Example 8

This example shows the steps for recovery of propionic acid from a dilute salt solution using a process of the present invention.

Precipitation of $CaCO_3$ Using TBA and $CO_2$:

22.42 gms of TBA was added to 100 mls of 0.6 molar $Ca(Pr)_2$ solution (106 gms/liter) and gassed with $CO_2$ for 30 min. A white precipitate of $CaCO_3$ formed and was filtered and weighed with a recovery of 90.8%.

Extraction of TBA/Pr:

A TBA/Pr amine/acid complex was prepared by mixing 199.92 gms of $H_2O$, 10.46 gms propionic acid, and 21.66 gms of TBA. 50 gms of the $H_2O$/TBA/HPr solution was mixed with 50 gms of each of n-butanol, n-pentanol and n-hexanol in three flasks, and separated in a separatory funnel. TBA/HPr in the organic phase was sampled and measured by the method of Ricker et al., 1979. The distribution coefficients for each of the three solvents were determined to be: n-butanol—1.39; n-pentanol—1.46; and n-hexanol—1.38.

Esterification of TBA/HPr in n-Hexanol:

A mixture of 325.44 gms n-hexanol, 74.48 gms of HPr, and 155.64 gms of TBA was prepared and introduced to the distillation apparatus as described in Example 10. An initial pot sample and a final pot sample after reaction were taken. Reaction time was about 12 hours not including heat up and cool down time. The pot temperature ranged from 157 C initially to 163 C at the end point. The samples were analyzed by the method of Ricker et al., 1979. The disappearance of HPr in the pot showed conversion to the ester of 92.2%.

Example 9

Figure 2:
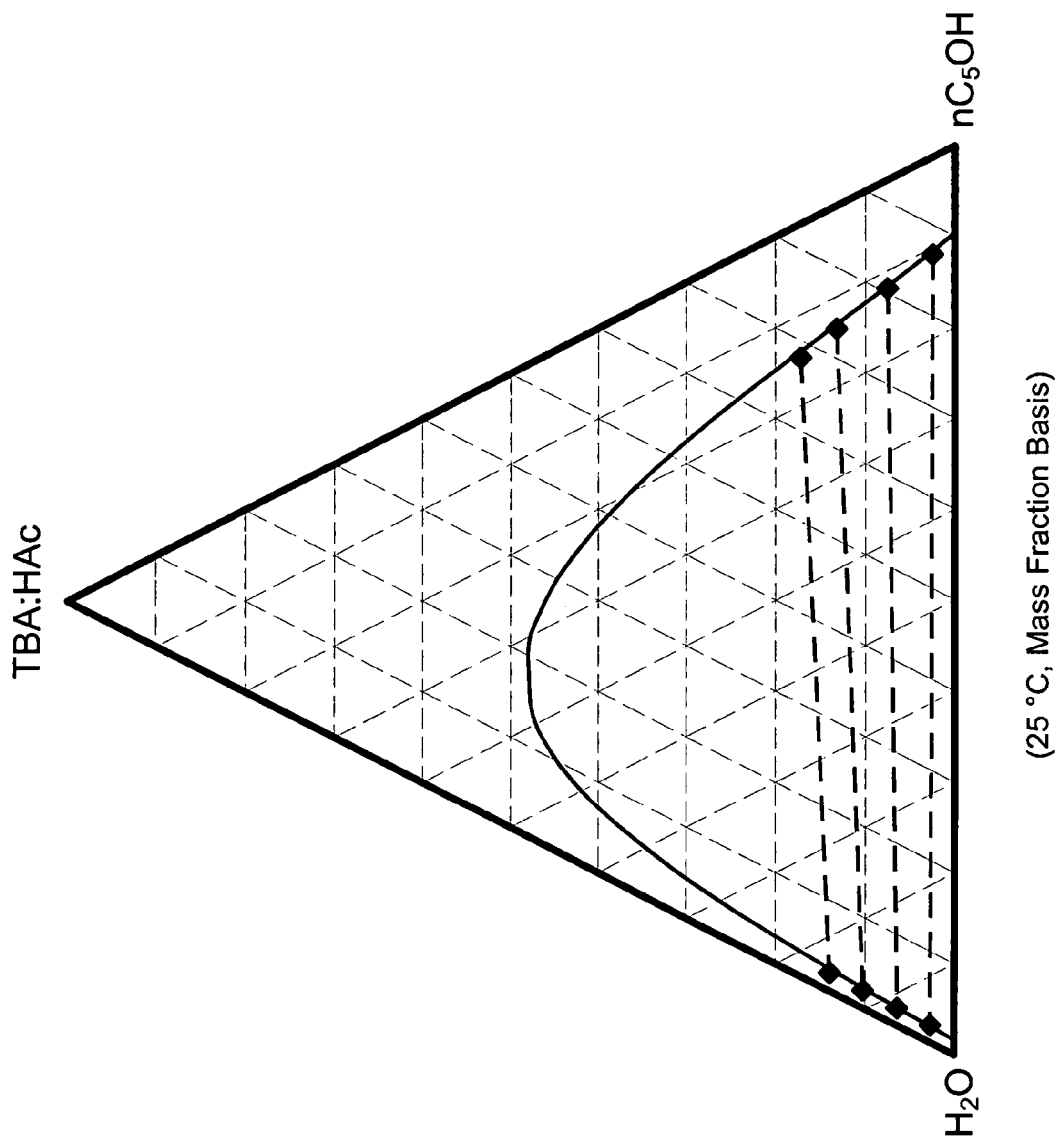
FIG. 2 is a phase diagram for n-pentanol, water and TBA: HAc complex.
Figure 3:
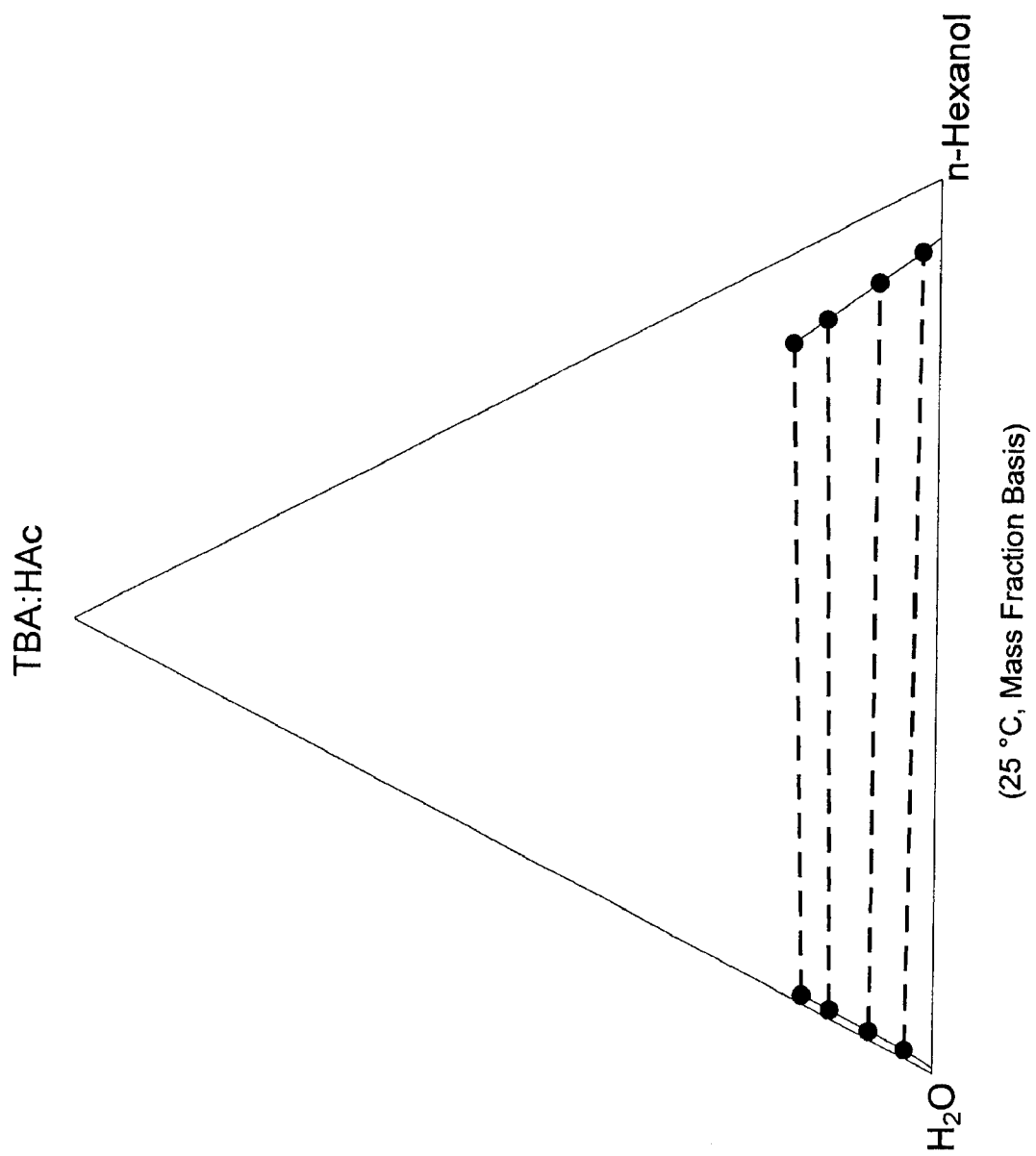
FIG. 3 is a phase diagram for n-hexanol, water and TBA: HAc complex.

This example shows liquid-liquid phase equilibrium diagrams constructed for n-pentanol and n-hexanol. FIGS. 2 and 3 are the experimentally measured phase diagrams. The tie lines are created by varying the starting concentration of the TBA:HAc concentration in a series of extractions as described above. The two phase regions are fairly broad and the tie-lines have a favorable slope. Distribution coefficients become more favorable at higher TBA:HAc concentrations. Only a few stages are needed to produce a concentrated TBA:HAc extract from a dilute aqueous solution.

Example 10

This example shows the production of an acid/solvent product between acetic acid and the four alcohol solvents of Example 7. The n-hexanol solvent was run with and without a sulfuric acid catalyst.

A simple distillation of alcohol solvent and the acid/amine complex was conducted at atmospheric pressure (~630 mm Hg) in a glass still consisting of a electric heating mantle, a 1 liter round bottom flask, a vacuum jacketed 30 cm distillation column packed with 4 mm×4 mm glass rings, and an overhead condenser and product splitter allowing the removal of a variable amount of distillate and return of reflux to the column. A two-step process was observed. Initially, the water dissolved in the extract was removed by azeotropic distillation using the alcohol itself as the drying solvent for the extract producing a dry solution of the amine complex in the alcohol solvent. The overhead splitter was configured so that the water was removed continuously as it was produced and the solvent was returned to the still as reflux. All of the alcohols tested form heterogeneous azeotropes with water and forming two liquid phases overhead.

Initial water removal rate was quite fast, only a few minutes. Then after the extract was dried, the distillation process was continued with total reflux of the solvent alcohol, and there was a continuous slow production of water overhead in the still usually over several hours. This water was produced from the esterification reaction of the alcohol solvent with the acid. Residual acetate in the still was measured by taking a sample from the still and measuring the acetate concentration by the method of Ricker et al., 1979 described above. The difference between the initial concentration and the sample at various times was taken to be the conversion to ester.

The esterification reactions were conducted in the setup described above, at atmospheric pressure (~630 mm Hg) for each of the solvents tested. 450 g of a room temperature solution containing a 3:1 molar ratio of alcohol to TBA:HAc complex were added to the still. The catalyzed run with n-hexanol included $H_2SO_4$ in the starting solution at a 0.1:1 mole ratio with respect to the TBA:HAc complex. The heating mantle was turned on and approximately thirty minutes later the solution began to boil. Water formed a second phase in the overheads as the reaction progressed. The water was collected and the volume recorded over time. Conversion was calculated as the percent of the maximum theoretical water if all of the acetic acid were converted to ester and confirmed by titration of residual TBA:HAc in the still pot samples. Ester formation was verified by gas chromatography using known ester samples as standards. The results of this experiment in terms of esterification yield are shown in Table 3.

TABLE 3

| Solvent | Esterification Yield at 4 hr, % Theoretical |
|---|---|
| n-Butanol | 12.6 |
| n-Pentanol | 38.1 |
| n-Hexanol | 82.7/93.6 |
| | (No Catalyst/$H_2SO_4$ Catalyst) |
| n-Octanol | 88.8 |

Figure 4:
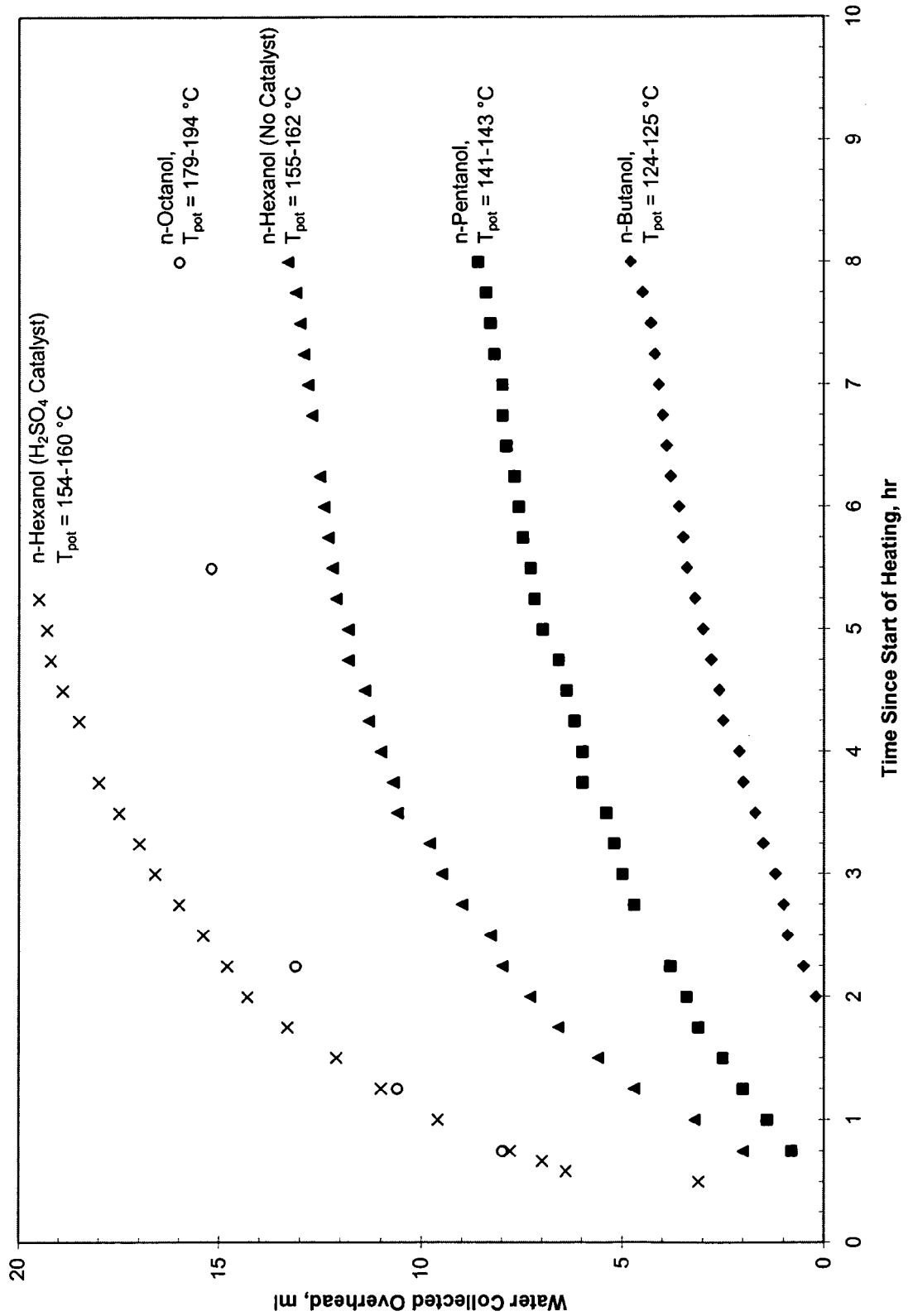
FIG. 4 plots the water generated during esterification in Example 8 and reports the observed range of pot temperatures.

FIG. 4 plots the water generated during esterification and reports the observed range of pot temperatures during the time the solutions were boiling. The pot temperature rose over time, further evidence of reaction. The curves in FIG. 4 are useful for comparing rates, but can only be qualitatively used to compare yield since different molar amounts of TBA:HAc were present in the starting solutions and differing amounts of materials were taken for samples over the course of the experiment. The values in Table 3 are more useful for comparing yields.

Both esterification rate and yield increased with increasing molecular weight of the alcohol. Rather than being related to the chain length of the alcohol, this improvement in performance was probably caused by the higher boiling point and thus higher reaction temperature for the higher molecular weight alcohols. Adequate esterification rate and yield could be achieved with the lower molecular weight alcohols if the reaction was conducted at elevated pressure. The pressures required are not extreme; for example, n-butanol will boil at 170° C. and 482.6 kPa, well within the range of industrial importance.

Esterification rate and yield can also be improved by using a catalyst. Comparison of the non-catalyzed n-hexanol run with the catalyzed run shows that sulfuric acid is potentially a good catalyst.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method for recovery of an organic acid from a dilute salt solution comprising an organic acid salt, the cation of which forms an insoluble carbonate salt, comprising:
   a. introducing a tertiary amine and $CO_2$ to the dilute salt solution to form an acid/amine complex and the insoluble carbonate salt;
   b. introducing a water immiscible solvent to the dilute salt solution to form a reaction phase comprising the acid/amine complex and the water immiscible solvent;
   c. continuously drying the reaction phase; and
   d. forming a product of the acid and the water immiscible solvent.

2. The method, as claimed in claim 1, wherein the water immiscible solvent is an alcohol.

3. The method, as claimed in claim 1, wherein the water immiscible solvent is an alcohol and the acid/solvent product is an ester.

4. The method, as claimed in claim 3, wherein the water immiscible solvent has a distribution coefficient of at least about 0.5.

5. The method, as claimed in claim 1, wherein the alcohol is selected from the group consisting of n-octanol, n-hexanol, n-pentanol, and n-butanol.

6. The method, as claimed in claim 1, wherein the water immiscible solvent is a mixed solvent comprising a solvent reactive with the acid portion of the acid/amine complex to form an acid/solvent product and a solvent that is inert with the acid portion of the acid/amine complex.

7. The method, as claimed in claim 1, wherein the water immiscible solvent has a distribution coefficient of at least about 0.5.

8. The method, as claimed in claim 1, wherein the water immiscible solvent has a distribution coefficient of at least about 0.75.

9. The method, as claimed in claim 1, wherein the water immiscible solvent has a distribution coefficient of at least about 1.

10. The method, as claimed in claim 1, wherein the water immiscible solvent has a selectivity value of at least about 8.

11. The method, as claimed in claim 1, wherein the water immiscible solvent has a selectivity value of at least about 15.

12. The method, as claimed in claim 1, wherein the water immiscible solvent has a selectivity value of at least about 20.

13. The method, as claimed in claim 1, wherein the tertiary amine is selected from the group consisting of tributylamine and dicyclohexyl methyl amine.

14. The method, as claimed in claim 1, wherein the organic acid is selected from the group consisting of acetic acid, lactic acid, propionic acid, butyric acid, succinic acid, citric acid, 3-hydroxypropionic acid, glycolic acid, and formic acid.

15. The method, as claimed in claim 1, wherein the step of continuously drying the reaction phase comprises a process selected from the group of removing water as an azeotrope with the solvent by azeotropic distillation and removing water by contacting the reaction phase with a water adsorbent.

16. The method, as claimed in claim 1, wherein the solvent is an alcohol and the step of forming the acid/solvent product comprises forming an ester between the acid and the alcohol by the production of water.

17. The method, as claimed in claim 1, wherein the water immiscible solvent is an alcohol and wherein the step of forming the acid/solvent product comprises adding a strong acid catalyst selected from the group consisting of a Lewis acid and a Brønsted acid catalyst to the solvent.

18. The method, as claimed in claim 1, wherein the water immiscible solvent is an alcohol and wherein the step of forming the acid/solvent product comprises adding a strong acid catalyst to the solvent, wherein the strong acid catalyst is selected from the group consisting of acid catalysts having a pKa less than the organic acid.

19. The method, as claimed in claim 18, wherein the strong acid catalyst is selected from the group consisting of sulfuric acid, hydrochloric acid and methane sulfonic acid.

20. The method, as claimed in claim 1, further comprising separating the acid/solvent product, the tertiary amine and the solvent.

21. The method, as claimed in claim 20, wherein the separated tertiary amine is used as the tertiary amine in step (a).

22. The method, as claimed in claim 20, wherein the separated solvent is used as the solvent in step (b).

23. The method, as claimed in claim 20, wherein the step of separating comprises distilling the acid/solvent product from the tertiary amine and the solvent.

24. The method, as claimed in claim 23, wherein the step of separating comprises distilling the solvent from the tertiary amine.

25. The method, as claimed in claim 20, wherein the solvent is an alcohol and the acid/solvent product is an ester and the method further comprises hydrogenating the ester to form an alcohol of the acid and regenerate the solvent alcohol.

26. The method, as claimed in claim 25, further comprising dehydrating the alcohol of the acid to form an olefin product.

27. The method, as claimed in claim 25, wherein the regenerated solvent is used as the solvent in step (b).

28. The method, as claimed in claim 25, wherein the solvent is an alcohol and the acid/solvent product is a first ester and the method further comprises transesterifying the first ester with a second alcohol to form a second ester.

29. The method, as claimed in claim 20, wherein the solvent is an alcohol and the acid/solvent product is an ester and the method further comprises hydrolyzing the ester to form the acid and regenerate the solvent alcohol.

30. The method, as claimed in claim 29, wherein the regenerated solvent is used as the solvent in step (b).

31. A method for recovery of an organic acid from a dilute salt solution comprising a calcium salt of an organic acid, comprising:
   a. introducing a tertiary amine and $CO_2$ to the dilute salt solution to form an acid/amine complex and calcium carbonate;
   b. mixing the dilute salt solution with a water immiscible alcohol having a distribution coefficient of at least about 0.5, whereby the acid/amine complex is extracted into the water immiscible alcohol;
   c. continuously drying the water immiscible alcohol; and
   d. forming an ester from the acid and the water immiscible alcohol to produce a mixture comprising the ester, residual water immiscible alcohol, and the tertiary amine.

32. A method for recovery of an organic acid selected from the group consisting of acetic acid, lactic acid, and propionic acid from a fermentation broth comprising a calcium salt of the organic acid, comprising:
   a. introducing a tertiary amine selected from the group consisting of tributylamine and dicyclohexyl methyl amine and $CO_2$ to the dilute salt solution to form an acid/amine complex and calcium carbonate;
   b. mixing the dilute salt solution with a water immiscible alcohol selected from the group consisting of octanol, hexanol, pentanol, and butanol, whereby the acid/amine complex is extracted into the water immiscible alcohol;
   c. continuously drying the water immiscible alcohol;
   d. forming an ester from the acid and the water immiscible alcohol to produce a mixture comprising the ester, residual water immiscible alcohol, and the tertiary amine;
   e. separating the ester, the tertiary amine and the water immiscible alcohol;
   f. using the separated tertiary amine as the tertiary amine in step (a);
   g. using the separated water immiscible alcohol as the water immiscible alcohol in step (b);
   h. treating the ester by a process selected from the group consisting of
      i. hydrogenating the ester to form an alcohol of the acid and regenerate the solvent alcohol; p2 ii. transesterifying the ester with a second alcohol to form a second ester;
      iii. hydrolyzing the ester to form the acid and regenerate the solvent alcohol.

33. A method for recovery of an organic acid from an acid/amine complex in an aqueous solution, comprising:
   a. introducing a water immiscible solvent to the aqueous solution to form a reaction phase comprising the acid/amine complex and the water immiscible solvent and an aqueous phase;
   b. continuously drying the reaction phase; and
   c. forming a product of the acid and the water immiscible solvent.

34. The method, as claimed in claim 17, wherein the acid catalyst is selected from the group consisting of a cationic ion exchange resin, a strong mineral acid, and a strong organic acid.

35. A method for recovery of an organic acid from a dilute salt solution comprising an organic acid salt, the cation of which forms an insoluble carbonate salt, comprising:
   a. introducing a tertiary amine and $CO_2$ to the dilute salt solution to form an acid/amine complex and the insoluble carbonate salt;
   b. introducing n-butanol to the dilute salt solution to form a reaction phase comprising the acid/amine complex and the n-butanol;
   c. continuously drying the reaction phase; and
   d. forming an ester of the acid and the n-butanol by adding a strong reactive acid catalyst to the solvent, said strong reactive acid catalyst selected from the group consisting of sulfuric acid, hydrochloric acid and methane sulfonic acid.

* * * * *

UNITED STATES PATENT AND TRADEMARK OFFICE
CERTIFICATE OF CORRECTION

PATENT NO. : 7,601,865 B2
APPLICATION NO. : 11/046206
DATED : October 13, 2009
INVENTOR(S) : Verser et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 619 days.

Signed and Sealed this

Fourteenth Day of December, 2010

David J. Kappos
*Director of the United States Patent and Trademark Office*